(12) United States Patent
Ginoux

(10) Patent No.: US 8,816,161 B2
(45) Date of Patent: Aug. 26, 2014

(54) MELON VARIETY NUN 01307 ME

(75) Inventor: Jean Paul Ginoux, Arles (FR)

(73) Assignees: Nunhems B.V., Nunhem (NL); Laboratoire ASL, Route de Graveson, Eyragues (FR)

( * ) Notice: Subject to any disclaimer, the term of this patent is extended or adjusted under 35 U.S.C. 154(b) by 88 days.

(21) Appl. No.: 13/544,005

(22) Filed: Jul. 9, 2012

(65) Prior Publication Data

US 2012/0315371 A1    Dec. 13, 2012

(51) Int. Cl.
*A01H 5/10* (2006.01)
*A01H 5/00* (2006.01)
*A01H 4/00* (2006.01)

(52) U.S. Cl.
USPC ............ 800/309; 800/260; 800/265; 800/266

(58) Field of Classification Search
None
See application file for complete search history.

(56) References Cited

PUBLICATIONS

UPOV descriptors, Guidelines for the Conduct of Tests for Distinctness, Uniformity and Stability, TG/18413 (Geneva 2001), as published by UPOV (International Union for the Protection of New Varieties and Plants, www.upov.int/en/publications/tg_rom/tg_index.html.
USDA descriptors are the plant variety descriptors for muskmelon/Cantaloupe (*Cucumis melo* L.) as published by the US Department of Agriculture, http://www.ams.usda.gov/AMSv1.0/getfile?dDocName=STELDEV3003780.
Jack E. Staub et al., Comparative analysis of cultivated melon groups (*Cucumis melo* L.) using random amplified polymorphic DNA and simple sequence repeat markers, Euphytica (2000) vol. 115, pp. 225-241.
Variety Tracer method of the Nak Tuinbouw (http://www.naktuinbouw.nl/en/topic/identification-using-dna), downloaded on Jul. 27, 2012.
Eugenia Martin et al., Identification of markers linked to agronomic traits in globe artichoke, Australian Journal of Crop Science (2008) vol. 1(2), pp. 43-46.

*Primary Examiner* — Brent T Page

(57) ABSTRACT

The invention relates to the field of *Cucumis melo*, in particular to a new variety of *Cucumis melo reticulatus*, NUN 01307 ME, plants and melon fruits; a sample of seed of said line having been deposited under Accession Number NCIMB 42204.

22 Claims, 1 Drawing Sheet

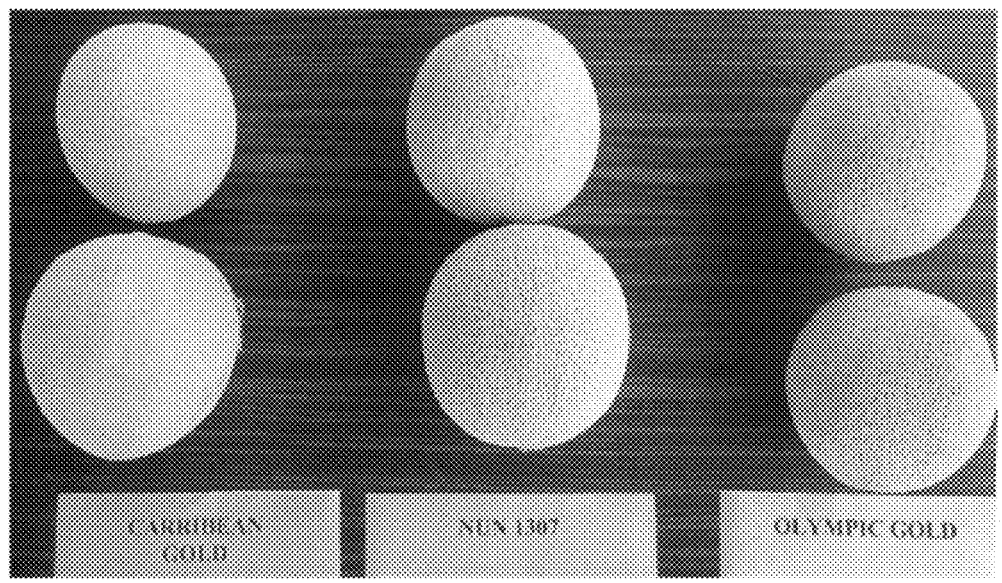

MELON VARIETY NUN 01307 ME

FIELD OF THE INVENTION

The present invention relates to the field of plant breeding. In particular, a new and distinct hybrid variety of melon is provided, designated NUN 01307 ME.

The new variety is a Common or Summer type (*Cucumis melo reticulatus*) with magenta flesh, netted rind, yellow-green primary rind color at edible maturity and a very spicy flavor.

Provided are seeds of NUN 01307 ME, plants and plant parts produced from these seeds such as harvested fruit or parts thereof, pollen, cells, leaves or parts thereof, petioles, shoots or parts thereof, stems or parts thereof, roots or parts thereof, cuttings or parts thereof, flowers, vegetative reproductions of the variety NUN 01307 ME, and progeny of the variety.

Melons or 'muskmelons', *Cucumis melo*, can be classified into: *C. melo cantalupensis*, *C. melo inodorous* and *C. melo reticulatus*.

*C. melo cantalupensis* are also referred to as Cantaloupes and are primarily round in shape with prominent ribs and almost no netting. Most have magenta, sweet flesh and they are usually very fragrant. In contrast to the European cantaloupe, the North American 'Cantaloupe' is not of this type, but belongs to the true muskmelons.

*C. melo reticulatus* is the true muskmelon, with reticulated skin (netted) and includes Galia melons, Sharlyn melons and the North American cantaloupe. It is also known as "rockmelon" or as "Common" or "Summer" type melon.

*C. melo inodorous* (or winter melons) can be subdivided into different types, such as Honeydew melon, Piel de Sapo, Sugar melon, Japanese melon, etc.

The Common melons or Summer melons are, as already mentioned, considered "true muskmelons" with reticulated skin. They have different flesh colors, such as creamy, yellow, green or orange-fleshed and are an excellent source of antioxidants such as beta-carotene and vitamin C.

Winter melons, (*C. melo inodorus*), have a hard rind which preserves freshness, include the well-known casaba, crenshaw and honeydew types. They are usually quite large with smooth or netted rinds and can be deep green, bright yellow, beige and many shades in between. They come in just about any shape imaginable. The flesh can be green, white, pale yellow or magenta and is usually incredibly sweet, but not very fragrant.

Honeydew melons are round to slightly oval shape and fruits at maturity of at least 1 kg (on average) or more. The flesh is usually pale green in color, while the smooth peel ranges from greenish to yellow. This fruit grows best in semi-arid climates and is harvested based on maturity. Maturity can be hard to judge, but is based upon ground color ranging from greenish white to creamy yellow. Quality is also determined by the honeydew having a surface free of scars or defects. Also, a honeydew should feel heavy for its size and have a waxy surface.

Sprite melon is a kind of melon, similar to honeydew, which originates from Japan. Since the late 1990s, it has been cultivated in North Carolina as a specialty crop and has increased in popularity in recent years. A sprite melon has a round shape and is typically about the size of a grapefruit (less than 700 g on average). The flesh of a sprite melon is ivory in color and firm, while the peel ranges from ivory (unripe) to yellowish (ripe). As the melon reaches optimal ripeness, horizontal brown markings will appear near the stem. The firm, juicy, sweet flesh of the sprite melon is usually eaten for dessert and tends to resemble the flavor of both pears and honeydew, however it is much sweeter than either of these and can often consist of 18% sugar.

The use of a type of melon is depending on a customer's preference for taste, color and aroma of the melon flesh. There is thus a need for a magenta fleshed Summer type of melon with unique flavor and aroma properties.

SUMMARY OF THE INVENTION

In one aspect of the invention, a seed of melon variety NUN 01307 ME is provided, wherein a representative sample of said seed has been deposited under Accession Number NCIMB 42204.

In another aspect the invention provides for a hybrid variety of *Cucumis melo reticulatus* called NUN 01307 ME. The invention also provides for a plurality of seeds of the new variety, plants produced from growing the seeds of the new variety. NUN 01307 ME, and progeny of any of these. Especially, progeny retaining one or more (or all, or all except one, two or three) of the "distinguishing characteristics" or one or more (or all, or all except one, two or three) of the "essential morphological and physiological characteristics" or of (essentially) all physiological and morphological characteristics of NUN 01307 ME referred to herein, are encompassed herein as well as methods for producing these.

In one aspect, such progeny have (essentially) all the physiological and morphological characteristics of melon variety NUN 01307 ME when grown under the same environmental conditions.

Further, a melon fruit produced on a plant grown from these seeds is provided.

In yet another embodiment of the invention, an Essentially Derived Variety of NUN 01307 ME having one, two or three physiological and/or morphological characteristics which are different from those of NUN 01307 ME and which otherwise has all the physiological and morphological characteristics of NUN 01307 ME, wherein a representative sample of seed of variety NUN 01307 ME has been deposited under Accession Number NCIMB 42204, is provided.

Further, a vegetatively propagated plant of variety NUN 01307 ME, or a part thereof, is provided having all the morphological and physiological characteristics of NUN 01307 ME when grown under the same environmental conditions.

Also a plant part derived from variety NUN 01307 ME is provided, wherein said plant part is selected from the group consisting of: harvested fruits or parts thereof, pollen, ovules, cells, leaves or parts thereof, petioles, shoots or parts thereof, stems or parts thereof, roots or parts thereof, cuttings, seeds, hypocotyl, cotyledon, flowers or parts thereof.

DEFINITIONS

"Melon" or "muskmelon" refers herein to plants of the species *Cucumis melo*. "Cultivated melon" refers to plants of *Cucumis melo* i.e. varieties, breeding lines or cultivars of the species *C. melo*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"Common" type or "Summer" type melon refers to melons of the *C. melo reticulatus* type.

"Netted" skin or rind refers to the presence of reticulate markings called 'netting' on the skin.

"UPOV descriptors" are the plant variety descriptors described for Muskmelon in the "Guidelines for the Conduct of Tests for Distinctness, Uniformity and Stability, TG/184/3 (Geneva 2001), as published by UPOV (International Union for the Protection of New Varieties and Plants, available on the world wide web at upov.int) and which can be downloaded from the world wide web at www.upov.int/en/publications/tg_rom/tg_index.html and is herein incorporated by reference in its entirety.

"USDA descriptors" are the plant variety descriptors for muskmelon/Cantaloupe (Cucumis melo L.) as published by the US Department of Agriculture, Agricultural Marketing Service, Science and Technology, Plant Variety Protection Office, Beltsville, Md. 20705 (available on the world wide web at www.ams.usda.gov/AMSv1.0/) and which can be downloaded from the world wide web at http://www.ams.usda.gov/AMSv1.0/getfile?dDocName=STELDEV3003780.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested fruits), plant cells, plant protoplasts, plant cell tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, seeds, clonally propagated plants, roots, stems, root tips, gratis, parts of any of these and the like. Also any developmental stage is included, such as seedlings, cuttings prior or after rooting, mature plants or leaves.

"Harvested plant material" refers herein to plant parts (e.g. fruits detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and morphological characteristics" means a plant having essentially all or all the physiological and morphological characteristics when grown under the same environmental conditions of the plant of NUN 01307 ME from which it was derived, e.g. the progenitor plant, the parent, the recurrent parent, the plant used for tissue- or cell culture, etc. For example, the plant may have all characteristics mentioned in Table 1. In certain embodiments, the plant having "essentially all the physiological and morphological characteristics" are plants having all the physiological and morphological characteristics, except for certain characteristics, such as one, two or three, mentioned, e.g. the characteristic(s) derived from a converted or introduced gene or trait and/or except for the characteristics which differ in an EDV. So, the plant may have all characteristics mentioned in Table 1, except for one, two or three characteristics of Table 1, in which the plant may thus differ.

A plant having one or more or all "essential physiological and/or morphological characteristics" or one or more "distinguishing characteristics" (such as one, two, three, four or five) refers to a plant having (or retaining) one or more, or all, or retaining all except one, two or three of the distinguishing characteristics mentioned in Table 1 when grown under the same environmental conditions that distinguish NUN 01307 ME from the most similar variety Caribbean Gold, or from the similar variety Olympic Gold, such distinguishing characteristics being selected from (but not limited to): later maturity (preferably needing at least about 4, 5, or 6 or more days from seeding to harvest); shorter leaf (Mature blade of third leaf) When using leaf of the (most) similar variety as reference, legs broad/narrower leaf (mature blade of third leaf) when using leaf of the (most) similar variety as reference; a yellow/green primary rind color at edible maturity whereas the primary rind color at edible maturity of Caribbean Gold is gray/green and the primary rind color at edible maturity of Olympic Gold is green (e.g., color chart value of primary rind color at edible maturity is 151 B for NUN 01307 ME whereas color chart values of primary rind color at edible maturity of Caribbean Gold or Olympic Gold is 190C or 139A, respectively); a magenta color of flesh of fruits at edible maturity of NUN 01307 ME near cavity and near center whereas the color of flesh of fruits at edible maturity of Caribbean Gold and Olympic Gold near cavity and near center is orange/salmon (e.g. color chart value of flesh of fruits at edible maturity of NUN 01307 ME near cavity and near center is 30A and color chart value of flesh of fruits at edible maturity of Caribbean Gold and Olympic Gold near cavity and near center is 25C); a very spicy flavor compared to a somewhat spicy flavor of similar variety Olympic Gold and mild flavor of most similar variety Caribbean. Gold; a reduced length of seed cavity (when using length of seed cavities of the (most) similar variety as reference); a reduced width of seed cavity when using width of seed cavities of the (most) similar variety as reference); and the amount of seeds per fruit is higher in fruits of NUN 01307 ME compared to varieties Caribbean Gold or Olympic Gold (e.g., at least about 10%, preferably are least about 15% or even at least about 20% when using amounts of seeds per fruits of the (most) similar variety as reference).

The physiological and/or morphological characteristics mentioned above are commonly evaluated at significance levels of 1%, 5%, 8% or 10% significance level, when measured under the same environmental conditions. For example, a progeny plant of NUN 01307 ME may have one or more (or all, or all except one, two or three) of the essential physiological and/or morphological characteristics of NUN 01307 ME listed in Table 1, or one or more or all (or all except one, two or three) of the distinguishing characteristics of NUN 001307 ME listed in Table 1 and above, as determined at the 1% or 5% significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering.

"Plant line" is for example a breeding line which can be used to develop one or more varieties.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, petiole, etc. When a whole plant is regenerated by vegetative propagation, it is also referred to as a vegetative propagation.

"Selfing" refers to self-pollination of a plant, i.e., the transfer of pollen from the anther to the stigma of the same plant. "Crossing" refers to the mating of two parent plants.

"Average" refers herein to the arithmetic mean.

"Locus" (plural loci) refers to the specific location of a gene or DNA sequence on a chromosome. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to, as homologous chromosomes. Diploid organisms have one copy of each gene (and therefore one allele) on each chromosome. If both alleles are the same, they are homozygotes. If the alleles are different, they are heterozygotes.

"Genotype" refers to the genetic composition of a cell or organism.

"Maturity" refers to the fruit developmental stage when the fruit has fully developed (reached its final size), begins to ripen and undergoes ripening, during which fruits can be divided into 1, 2, 3 or more maturity stages. Thereafter, fruits become overripe. In particular embodiments "maturity" is defined as the mature stage of fruit development and optimal time for harvest. In one embodiment a "mature" melon is defined as having reached the stage of maturity which will insure the proper completion of the normal ripening process. In particular embodiments, fruit should be harvested at a maturity stage i.e. substantially near maximum sweetness and flavor intensity.

"Harvest maturity" is referred to as the stage at which a melon fruit is ripe or ready for harvest or the optimal time to harvest the fruit. In one embodiment, harvest maturity is the stage which allows proper completion of the normal ripening.

"Abscission zone" is the layer or zone separating the fruit from the peduncle.

"Cavity" or "seed cavity" is the center of the fruit containing the maternal tissues and seeds.

"Flavor" refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, etc.).

"Aroma" refers to smell (or odor) characteristics of melon fruits or fruit parts (fruit flesh).

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated NUN 01307 ME. Progeny may be derived by regeneration of cell culture or tissue culture or parts of a plant designated NUN 01307 ME or selfing of a plant designated NUN 01307 ME or by producing seeds of a plant designated NUN 01307 ME. In further embodiments, progeny may also encompass plants derived from crossing of at least one plant designated NUN 01307 ME with another melon plant of the same or another variety or (breeding) line, or with a wild melon plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained froth, obtainable from or derivable from the former generation by, e.g., traditional breeding methods, regeneration or genetic transformation techniques. For example, a second generation progeny can be produced from a first generation progeny by any of the methods mentioned above. Especially progeny of NUN 01307 ME which are EDVs or which retain all (or all except 1, 2 or 3) physiological and/or morphological characteristics of NUN 01307 ME listed in Table 1, or which retain all (or all except 1, 2, or 3) of the distinguishing characteristics of NUN 01307 ME described elsewhere herein and in Table 1, are encompassed herein.

The terms "gene converted" or "conversion plant" in this context refer to melon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a melon variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a melon plant by transformation. A plant comprising a transgene stably integrated into its genome is referred to as "transgenic plant".

The term "mean" refers to the arithmetic mean of several measurements. The skilled person understands that the appearance of a plant depends to some extent on the growing conditions of said plant. Thus, the skilled person will know typical growing conditions for Summer melons described herein. The mean, if not indicated otherwise within this application, refers to the arithmetic mean of measurements on at least 10 different, randomly selected plants of a variety or line.

DRAWINGS

The drawings described herein are for illustration purposes only and are not intended to limit the scope of the present teachings in any way.

FIG. 1 shows melon fruits at edible maturity with different rind color of NUN 01307 ME, of most similar comparison varieties Caribbean Gold and of similar comparison variety Olympic Gold (longitudinal axis).

DETAILED DESCRIPTION

A *C. melo reticulatus* is a true muskmelon, with reticulated skin (netted) and includes Galia melons, Sharlyn melons and the North American cantaloupe. A number of characteristics are important to melon breeders including (but not limited to) (a) the fruit length; (b) the fruit diameter; (c) the fruit weight; (d) the fruit brix; and (e) rind thickness.

The present invention relates to a *Cucumis melo reticulatus* melon type, referred to as NUN 01307 ME, or progeny or EDVs thereof, which has magenta-colored flesh, netted rind, a yellow-green primary rind color at edible maturity and a very spicy flavor and which is most similar to Caribbean Gold, a commercial variety of Rijk Zwaan. For example, the flesh color of the fruits at edible maturity of the melon plants according to the invention has on the Royal Horticultural Society (RHS) color chart a value of RHS 30A or similar color values while the flesh color of most similar Caribbean Gold (or similar variety Olympic Gold) has a value of RHS 25C or similar color values. In addition, the new magenta-fleshed melon type has a refractometer % of soluble solids (degrees brix) (i.e. of about 14.3% soluble solids) compared to most similar Caribbean Gold (having a somewhat higher brix value of about 14.8% soluble solids) and similar variety Olympic Gold (having a lower brix value of about 12.6% soluble solids), no aroma compared to similar variety Olympic Gold having a faint aroma, and a very spicy flavor compared with a mild flavor of most similar variety Caribbean Gold and a somewhat spicy flavor of similar variety Olympic Gold.

Furthermore, the new variety differs from similar variety Olympic Gold, e.g., in the color of leaf i.e medium green versus dark green for similar variety Olympic Gold, and in that the melon fruit of the invention has a larger diameter of about 13.1 cm compared to the most similar variety Caribbean Gold and similar variety Olympic Gold (having an average fruit diameter of about 12.3 cm and 12.4 cm, respectively), has a yellow/green primary rind color at edible maturity (e.g. RHS 151B) which changes to orange (e.g., RHS 17C) at full maturity, while that of Olympic Gold changes from green (RHS 139A) to orange (e.g., RHS N25D) and that of most similar variety Caribbean Gold changes from gray/green (RHS 190C) to buf (e.g. RHS 160D).

Variety NUN 01307 ME provided herein differs from the most similar comparison variety Caribbean Gold and from the similar comparison variety Olympic Gold, when grown under the same environmental conditions, in one or more characteristics (referred herein to as "distinguishing characteristics" or "distinguishing morphological and/or physiological characteristics" (or essential physiological and/or morphological characteristics) selected from:

Earliness (maturity), i.e. NUN 01307 ME requires significantly more days from seeding to harvest maturity when using days from seeding to harvest maturity of the most similar variety Caribbean Gold, or of similar variety Olympic Gold, as reference. In other words, when grown under the same environmental conditions, NUN 01307 ME requires (on average) at least about 4, 5, 6, or more days from seeding to harvest maturity than Caribbean Gold or Olympic Gold, e.g. NUN 01307 ME requires around 92 days from seeding to harvest maturity while most similar variety Caribbean Gold requires around 80 days from seeding to harvest maturity or similar variety Olympic Gold requires around 86 days from seeding to harvest maturity, respectively;

Length of leaf (average length of the mature blade of the third leaf) of NUN 01307 ME is shorter than the third leaf of Caribbean Gold or Olympic Gold such as at least about 10% shorter when using the third leaf of most similar variety Caribbean Gold or similar variety Olympic Gold as reference. For example, the third leaf of NUN 01307 ME is at least about 14 mm shorter than the third leaf of Caribbean Gold or Olympic Gold (NUN 01307 ME: 105.5 mm; Caribbean Gold: 120.3 mm; Olympic Gold: 123.2 mm);

Width of leaf (average width of the mature blade of the third leaf) of NUN 01307 ME is less broad/narrower than the third leaf of Caribbean Gold or Olympic Gold when using leaf width of most similar variety Caribbean Gold or similar variety Olympic Gold as reference. For example, width of the third leaf of NUN 01307 ME is at least about 7.5 mm shorter than that of the third leaf of Caribbean Gold or Olympic Gold (NUN 01307 ME: 132.3 mm; Caribbean Gold: 142.2 mm; Olympic Gold: 140.3 mm);

Primary rind color at edible maturity, i.e. NUN 01307 shows a yellow/green primary rind color at edible maturity whereas the primary rind color at edible maturity of Caribbean Gold is gray/green and the primary rind color at edible maturity of Olympic Gold is green (e.g., color chart value of primary rind color at edible maturity is 151B for NUN 01307 whereas color chart values of primary rind color at edible maturity of Caribbean Gold or Olympic Gold is 190C or 139A, respectively)

Color of flesh of fruits at edible maturity, i.e. the color of flesh of fruits at edible maturity of NUN 01307 ME near cavity and near center is magenta whereas the color of flesh of fruits at edible maturity of most similar comparison variety Caribbean Gold and similar comparison variety Olympic Gold near cavity and near center is orange/salmon (e.g. color chart value of flesh of fruits at edible maturity of NUN 01307 ME near cavity and near center is 30A whereas color chart value of flesh of fruits at edible maturity of Caribbean Gold and Olympic Gold near cavity and near center is 25C);

Flavor, i.e. NUN 01307 ME has a very spicy flavor compared to a somewhat spicy flavor of Olympic Gold and mild flavor of most similar variety Caribbean Gold;

Length of seed cavities, i.e. NUN 01307 ME has a reduced length of seed cavity compared with the length of seed cavities of Caribbean Gold or Olympic Gold when using length of seed cavities of most similar comparison variety Caribbean Gold or similar comparison variety Olympic Gold as reference. For example, the average length of seed cavities of NUN 01307 ME is at least about 7 mm shorter compared to seed cavities of Caribbean Gold or Olympic Gold (e.g., length of seed cavities of NUN 01307 ME: 80.9 mm, of Caribbean Gold: 92.8 mm, of Olympic Gold: 88.2 mm);

Width of seed cavities, i.e. NUN 01307 ME has a narrower seed cavity when using width of seed cavities of the (most) similar variety as reference. For example, the width of seed cavities of NUN 01307 ME is at least about 6 mm narrower compared to seed cavities of Caribbean Gold or Olympic Gold (e.g., width of seed cavities of NUN 01307 ME: 50.8 mm, of Caribbean Gold: 60.6 mm, of Olympic Gold: 57.1 mm);

Seeds per fruit, i.e. the average number of seeds per fruit is higher in fruits of NUN 01307 ME compared to the number of seeds in comparison variety Caribbean Gold or Olympic Gold such as the number of seeds is preferably at least about 10%, more preferably at least about 20% higher in fruits of NUN 01307 EM compared to fruits of comparison variety Caribbean Gold or Olympic Gold when using the amount of seeds per fruits of the (most) similar variety as reference. For example, the number of seeds per fruit of NUN 01307 EM is at least about 80, preferably at least about 100, more preferably at least about 120 seeds higher in fruits of NUN 01307 EM compared to fruits of comparison variety Caribbean Gold or Olympic Gold (amount of seeds per fruit of NUN 01307 EM: 600, of Caribbean Gold: 480, of Olympic Gold: 461).

Fruit shape, i.e. fruits of NUN 01307 ME are slightly rounder compared to fruits of comparison variety Caribbean Gold or Olympic Gold when using fruit shape as reference. For example fruits of NUN 01307 have a length/width ratio of about 13.4/13.1 while fruits of comparison variety Caribbean Gold and Olympic Gold have a ratio of about 13.7/12.3 and 13.8/12.4, respectively.

It is understood that "significant" differences refer to statistically significant differences, when comparing the characteristic between two plant lines or varieties when grown under the same conditions. Preferably at least about 10, 15, 20 or more plants per line or variety are grown under the same conditions and characteristics are measured on at least about 10, 15, 20 or more randomly selected plant or plant parts to obtain averages. Thus, physiological and morphological characteristics or traits are commonly evaluated at a significance level of 1%, 5%, 8% or 10%, when measured in plants grown under the same environmental conditions. For example, two replications of 50 plants each, from which 20 plants or plant parts were randomly selected can be used to measure characteristics.

In one aspect, the invention provides seeds of the melon variety designated NUN 01307 ME wherein a representative sample of seeds of said variety was deposited under the Budapest Treaty, with Accession number NCIMB 42204.

Seeds of NUN 01307 ME are obtainable by crossing the male parent with the female parent and harvesting the seeds produced on the female parent. The resultant NUN 01307 ME seeds can be grown to produce NUN 01307 ME plants. In one embodiment a plurality of NUN 01307 ME seeds are packaged into small and/or large containers (e.g., bags, cartons, cans, etc.). The seeds may be primed and/or treated with various compounds, such as seed coatings and/or fungicides and/or insecticides.

Also provided are plants of melon variety NUN 01307 ME, or a fruit or other plant part thereof, produced from seeds, wherein a representative sample of said seeds has been deposited under the Budapest Treaty, with Accession Number NCIMB 42204. Also included is a cell culture or tissue culture produced from such a plant or a plant regenerated from such a cell culture or tissue culture, said plant expressing all the morphological and physiological characteristics of NUN 01307 ME, or all except one, two or three of the morphological and physiological characteristics of NUN 01307 ME. In one embodiment said plant expressed all the distinguishing characteristics of NUN 01307 ME, or all the distinguishing characteristics except one, two or three thereof. Plants of NUN 01307 ME can be produced by seeding directly in the ground (e.g., field) or by germinating the seeds in controlled environment conditions (e.g., greenhouses) and then transplanting the seedlings into the field. For example by sowing the seed into prepared seed beds where they will remain for the entire production of the crop. Alternatively, the melon seed may be planted through a black plastic mulch. The dark plastic will absorb heat from the sun, warming the soil early. It will also help to conserve moisture during the growing season, controls weeds and makes harvesting easier and cleaner. See for example www.anrcatalog.ucdavis.edu for cultivation, harvesting, handling and postharvest methods commonly used.

In another aspect, the invention provides for a melon plant of melon variety NUN 01307 ME, a representative sample of seed from said variety has been deposited under the Budapest Treaty, with Accession number NCIMB 42204.

In other aspects, the invention provides for a fruit of melon variety NUN 01307 ME, or a plant part, such as pollen, flowers, shoots or cuttings of variety NUN 01307 ME or parts thereof.

In still another aspect the invention provides a method of producing a melon plant, comprising crossing a plant of melon variety NUN 01307 ME with a second melon plant one or more times, and selecting progeny from said crossing.

In yet another aspect the invention provides a method of producing a melon plant, comprising selling a plant of melon variety NUN 01307 ME one or more times, and selecting progeny from said selling.

In other aspects, the invention provides for progeny of variety NUN 01307 ME such progeny obtained by further breeding NUN 01307 ME. Further breeding NUN 01307 ME includes selling NUN 01307 ME one or more times and/or cross-pollinating NUN 01307 ME with another melon plant or variety one or more times. In particular, the invention provides for progeny that retain all (or all except one, two or three) of the essential morphological and physiological characteristics of NUN 01307 ME or that retain one or more or all (or all except one, two or three) of the distinguishing characteristics of the melon type described further above and when grown under the same environmental conditions. In another aspect, the invention provides for vegetative reproductions of the variety NUN 01307 ME, or of progeny thereof, and the invention also provided for essentially derived varieties (EDVs) of NUN 01307 ME, or of progeny thereof, and vegetative reproductions of such EDVs.

The morphological and/or physiological differences between plants according to the invention, i.e. NUN 01307 ME or progeny thereof, or an EDV thereof, and other known varieties can easily be established by growing NUN 01307 ME (or progeny or EDVs) next to the other varieties (in the same field, under the same environmental conditions), preferably in several locations which are suitable for said melon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07' 261"/W 121 degrees 18' 807", USA, whereby e.g. type of melon, area of best adaptation in USA, days from seeding to harvest, plant fertility, plant habit, leaf shape, leaf lobes, leaf color, leaf length, width and surface, fruit length, fruit diameter, fruit weight, fruit shape, fruit surface, blossom scar, rib presence and number of ribs per fruit, rib width, rib surface, suture depth, suture surface, shipping quality, fruit abscission, rind net presence/distribution/coarseness/interlacing/interstices, rind firmness (texture), rind thickness, rind color at edible maturity, mottling color, net color, furrow (suture), rind color at full maturity, mottling color, net color, furrow (suture), flesh color near cavity, flesh color in center, flesh color near rind, % soluble solids, flesh aroma, flesh flavor, flesh firmness (texture), seed cavity length, seed cavity width, seed cavity shape, number of seeds per fruit, weight per 1,000 seeds, disease resistances and/or insect resistances can be measured and directly compared.

Morphological and/or physiological characteristics (and distinguishing characteristics which distinguish NUN 01307 ME from Caribbean Gold and/or Olympic Gold) of NUN 01307 ME, are provided in the Examples, in Table 1. Encompassed herein are also plants derivable from NUN 01307 ME (e.g. by selfings and/or crossing and/or backcrossing with NUN 01307 ME and/or mutant selection and/or natural variant selection and/or progeny thereof) comprising all (or all except one, two or three) of the physiological and/or morphological characteristics of NUN 01307 listed in Table 1 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of fruits can be compared, such as cold storage holding quality (browning), post-harvest rind firmness and/or flesh firmness, and juiciness can be measured using known methods. Flesh firmness can for example be measured using a penetrometer, e.g. by inserting a probe into the fruit flesh and determining the insertion force; or other methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (http://www.rhs.org.uk/Plants/RHS-Publications/RHS-colour-charts).

In a preferred embodiment, the invention provides for melon fruits of variety NUN 01307 ME, or a part of the fruit. In another embodiment, the invention provides for a container comprising or consisting of a plurality of harvested melon fruits of NUN 01307 ME, or progeny thereof, or a derived variety, such as an EDV.

In yet a further embodiment, the invention provides for a method of producing a new melon plant. The method comprises crossing a plant of the invention NUN 01307 ME or an EDV thereof or a progeny plant thereof, either as male or as female parent, with a second melon plant (or a wild relative of melon) one or more times, and/or selfing a melon plant according to the invention i.e. NUN 01307 ME or an EDV thereof or a progeny plant thereof, one or more times, and selecting progeny from said crossing and/or selfing. The second melon plant may be any C. melo, but in one embodiment the second melon plant is of the species C. melo reticulatus, e.g. another Summer type melon line or variety.

Progeny are either the generation (seeds) produced from the first cross (F1) or selfing (S1), or any further generation produced by crossing and/or selfing (F2, F3, etc.) and/or backcrossing (BC1, BC2, etc.) one or more selected plants of the F1 and/or S1 and/or BC1 generation (or plants of any further generation, e.g. the F2) with another melon plant (and/or with a wild relative of melon). Progeny may have all (or all except one, two or three) of the physiological and/or morphological characteristics of melon variety NUN 01307 ME when grown under the same environmental conditions and/or progeny may have (be selected for having) one or more, or all (or all except one, two or three) of the distinguishing characteristics of melons of the invention. Using common breeding methods such as backcrossing or recurrent selection, one or more specific characteristics may be introduced into NUN 01307 ME, to provide an EDV of NUN 01307 ME.

The invention provides for methods of producing varieties which retain all (or all except one, two or three) of the morphological and/or physiological characteristics of NUN 01307 ME or that retain all (or all except one, two or three) of the distinguishing characteristics of NUN 01307 ME. The invention provides also for methods of producing EDVs (Essentially Derived Varieties) of NUN 01307 ME which differ from NUN 01307 ME in one, two, three or more morphological and/or physiological characteristics, but which are still genetically closely related to NUN 0130TME. The relatedness can, for example be determined by fingerprinting techniques (e.g., making use of isozyme markers and/or molecular markers such as SNP markers, AFLP markers, microsatellites, SSR markers, minisatellites, RAPD markers, RFLP markers and others). A plant is "closely related" to NUN 01307 ME if its DNA fingerprint is at least 80%, 90%, 95% or 98% identical to the fingerprint of NUN 01307 ME. In one embodiment AFLP markers are used for DNA fingerprinting (Vos et al. 1995, Nucleic. Acid Research 23: 4407-4414) or other markers, such as microsatellite markers. A closely related plant may have a Jaccard's Similarity index of at least about 0.8, preferably at least about 0.9, 0.95, 0.95, 0.96, 0.97, 0.98 or more (Staub et al 2000, Euphytica 115: 225-241). The invention also provides plants and varieties obtained by these methods. In one embodiment, relatedness and whether a variety is an EDV of NUN 01307 ME, may be determined according to the Variety Tracer method of the Nak Tuinbouw (http://www.naktuinbouw.nl/en/topic/identification-using-dna).

By crossing and/or selfing also (one or more) single traits may be introduced into the variety of the invention i.e. NUN 01307 ME (e.g., using backcrossing breeding schemes), while retaining the remaining morphological and/or physiological characteristics of NUN 01307 ME and/or while retaining one or more (or all except one, two or three) of the distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 01307 ME by breeding with NUN 01307 ME.

Any pest or disease resistance genes may be introduced into a plant according to the invention, i.e. NUN 01307 ME, progeny thereof or into an EDV of NUN 01307 ME. Resistance to one or more of the following diseases is preferably introduced into plants of the invention: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporuni* f.sp. *melonis* (Fom) race 2, *Fusarium oxysporum* f.sp. *melonis* (Fom) race 1-2 *Fusarium* Wilt R2, Root Knot (Nematode), Anthracnose, Cucumber Mosiac, and Squash Mosaic.

Resistance to one or more of the following pests is preferably present or introduced into plants of the invention: Aphid resistance, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer. Other resistance genes, against pathogenic viruses, fungi, bacteria or pests may also be introduced.

Thus, invention also provides a method for developing, an melon plant in a melon breeding program, using a melon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 01307 ME or progeny thereof, or an EDV thereof, with a different melon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion, into a melon plant according to the invention and/or into NUN 01307 ME comprising:
(a) crossing a melon plant of variety NUN 01307 ME, a representative sample of seed of said variety having been deposited under Accession Number NCIMB 42204, with a second melon plant comprising a desired single locus to produce F1 progeny plants;
(b) selecting F1 progeny plants that have the single locus to produce selected F1 progeny plants;
(c) crossing the selected progeny plants with a plant of NUN 01307 ME, to produce backcross progeny plants;
(d) selecting backcross progeny plants that have the single locus and one or more or all (or all except one, two or three) of the distinguishing characteristics of melons according to the invention and/or all (or all except one, two or three) of the physiological and/or morphological characteristics of NUN 01307 ME to produce selected backcross progeny plants; and
(e) repeating steps (c) and (d) one or more times in succession to produce selected second, third, fourth or higher backcross progeny plants that comprise the single locus and otherwise one or more or all distinguishing characteristics of the melons according to the invention and/or comprise all of the physiological and morphological characteristics of NUN 01307 ME, when grown in the same environmental conditions.

The above method is provided, wherein the single locus confers a trait, wherein the trait is pest resistance or disease resistance.

In one embodiment the trait is disease resistance and the resistance is conferred to Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f.sp. *melonis* (Fom) race 0, *Fusarium oxysporum* f.sp. *melonis* (Fom) race 1, *Fusarium oxysporum* f.sp. *melonis* (Fom) race 0.2, *Fusarium oxysporum* f.sp. *melonis* (Fom) race 1-2, *Fusarium* Wilt R2, Root Knot (Nematode); Anthracnose, Cucumber Mosiac, or Squash Mosaic.

In one embodiment the trait is pest resistance and the resistance is conferred to Aphid, Pickle Worm, Darkling Ground Beetle, Banded Cucumber Beetle, Mite, Western Spotted Cucumber Beetle, Melon Leafhopper, Melon Worm, Western Striped Cucumber Beetle or Melon Leafminer.

The invention also provides a melon plant comprising at least a first set of the chromosomes of melon line NUN 01307 ME, a sample of seed of said line having been deposited under Accession Number NCIMB 42204; further provided is a melon plant comprising a single locus conversion, wherein said melon plant has essentially all of the morphological and/or physiological characteristics of the melon plant comprising at least a first set of the chromosomes of melon variety NUN 01307 ME. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 01307 ME may also be mutated (by e.g. irradiation, chemical mutagenesis, heat treatment, etc.) and mutated seeds or plants may be selected in, order to change one or more characteristics of NUN 01307 ME, e.g. one, two, three or more of the essential physiological and/or morphological characteristics of NUN 01307 ME may be changed. The one, two, three or more changed characteristics may be one, two or three of the distinguishing characteristics of NUN 01307 ME. Also natural mutants or natural variants of NUN 01307 ME may be identified and used in breeding. Methods such as TILLING and/or EcoTILLING may be applied to melon populations in order to identify mutants. Similarly, NUN 01307 ME may be transformed and regenerated, whereby one or more chimeric genes are introduced into the variety or progeny thereof or into an EDV thereof. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc can be introduced into NUN 01307 ME, or progeny thereof, by transforming NUN 01307 ME or progeny thereof with a transgene that confers the desired trait, wherein the transformed plant retains all the phenotypic and/or morphological and/or physiological characteristics of NUN 01307 ME or the progeny thereof and contains the desired trait. Thus, also a transgenic melon plant comprising a transgene conferring a desired trait and further comprising all (or all except one two or three) of the morphological and/or physiological characteristics of NUN 01307 ME, or further comprising all (or all except one, two or three) of the distinguishing characteristics of NUN 01307 ME, is provided herein.

The invention also provides for progeny of melon variety NUN 01307 ME obtained by further breeding with NUN 01307 ME. In one aspect progeny are F1 progeny obtained by crossing NUN 01307 ME with another plant or S1 progeny obtained by selfing NUN 01307 ME. Also encompassed are F2 progeny obtained by selfing the F1 plants. "Further breeding" encompasses traditional breeding (e.g., selfing, crossing, backcrossing), marker assisted breeding, and/or mutation breeding. In one embodiment, the progeny have one or more or all of the distinguishing characteristics mentioned further above when grown under the same environmental conditions. In a further embodiment the progeny have all the physiological and morphological characteristics of variety NUN 01307 ME when grown under the same environmental conditions. In another embodiment the progeny are EDVs and/or have one, two, or three distinct traits (qualitative or quantitative) introduced into NUN 01307 ME, while retaining all the other physiological and morphological characteristics of variety NUN 01307 ME when grown under the same environmental conditions.

An EDV is an Essentially Derived Variety of NUN 01307 ME having one, two or three physiological and/or morphological characteristics which are different from those of NUN 01307 ME and which otherwise has all the physiological and morphological characteristics of NUN 01307 ME, wherein a representative sample of seed of variety NUN 01307 ME has been deposited under Accession Number NCIMB 42204. In particular variants which differ from NUN 01307 ME in one, two or three of the characteristics mentioned in Table 1 are encompassed.

In one aspect, the EDV differs from NUN 01307 ME in one, two or three of the distinguishing morphological and/or physiological characteristics selected from: i) earliness, ii) leaf length, iii) leaf width, iv) primary rind color at edible maturity, v) flesh color at edible maturity near cavity and near center, vi) fruit flavor, vii) length of the seed cavity, viii) width of the seed cavity, ix) number of seeds per fruit, x) fruit shape (length/width ratio).

In another embodiment the EDV may differ from NUN 01307 ME in one, two or three morphological and/or physiological characteristic other than the "distinguishing morphological and/or physiological characteristics" (or essential physiological and/or morphological characteristics) of NUN 01307 ME for example selected from (but not limited to): i) leaf shape, ii) rind texture, iii) rind thickness at medial, or other characteristics.

Melons according to the invention, such as the variety NUN 01307 ME, or its progeny or an EDV of NUN 01307 ME, can also be reproduced using vegetative reproduction methods. Therefore, the invention provides for a method of producing plants, or a part thereof, of variety NUN 01307 ME, or of progeny thereof, or of an EDV of NUN 01307 ME, comprising vegetative propagation of variety NUN 01307 ME or of progeny thereof, or of an EDV of NUN 01307 ME. Vegetative propagation comprises regenerating a whole plant from a part of variety NUN 01307 ME (or from its progeny or from an EDV of NUN 01307 ME), such as a cutting, a cell culture or a tissue culture.

The invention also provides for a vegetatively propagated plant of variety NUN 01307 ME (or from its progeny or from an EDV of NUN 01307 ME), or a part thereof, having one or more distinguishing characteristics and/or all the morphological and physiological characteristics of NUN 01307 ME (except for the characteristics differing in the EDV), when grown under the same environmental conditions.

Parts of NUN 01307 ME (or from its progeny or from an EDV of NUN 01307 ME) encompass any cells, tissues, organs obtainable from the seedlings or plants, such as but not limited to: melon fruits or parts thereof, cuttings, hypocotyl, cotyledon, pollen, flowers, anthers, embryos, ovaries, and the like. Such parts can be stored and/or processed further. Encompassed are therefore also food or feed products comprising one or more of such parts, such as canned melon fruit parts, fresh melon fruit parts, etc. from NUN 01307 ME or from progeny thereof, or from a derived variety, such as an EDV.

In one aspect, haploid plants and/or double haploid plants of NUN 01307 ME, or an EDV of NUN 01307 ME, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 01307 ME (or from its progeny or from an EDV of NUN 01307 ME), or from a vegetatively propagated plant of NUN 01307 ME (or from its progeny or from an EDV of NUN 01307 ME), being selected from the group consisting of: harvested fruits or parts thereof, pollen, cells, leaves or parts thereof, petioles, cotyledons, hypocotyls, shoots or parts thereof, stems or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

The invention also provides for a food or feed product comprising or consisting of a plant part described herein preferably a melon fruit or part thereof and/or an extract from a plant part described herein. The food or feed product may be fresh or processed, e.g., canned, steamed, boiled, fried, blanched and/or frozen, etc.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable melon fruits are generally sorted by size and quality after harvest.

All documents (e.g., patent publications) are herein incorporated by reference in their entirety.

EXAMPLES

Development of NUN 01307 ME

The hybrid NUN 01307 ME was developed from a male and female proprietary inbred line of Nunhems. The female and male parents were crossed to produce hybrid (F1) seeds of NUN 01307 ME. The seeds of NUN 01307 ME can be grown to produce hybrid plants and parts thereof (e.g. melon fruit). The hybrid NUN 01307 ME can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 01307 ME is uniform and stable.

DEPOSIT INFORMATION

A total of 2500 seeds of the hybrid variety NUN 01307 ME were deposited according to the Budapest Treaty by Nunhems B.V. on Jan. 14, 2014, at the NCIMB Ltd., Ferguson Building, Craibstone Estate, Bucksburn, Aberdeen AB21 9YA, United Kingdom (NCIMB). The deposit has been assigned Accession Number NCIMB 42204.

A deposit of NUN 01307 ME and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

"USDA descriptors" are plant variety descriptors described for melon in the "Objective Description of Variety Muskmelon/Cantaloupe (*Cucumis melo* L.)—Exhibit C" of the U.S. Department of Agriculture, Agricultural Marketing Service, Science and Technology, Plant Variety Protection Office, Beltsville, Md. 20705, which can be downloaded from http://www.ams.usda.gov/AMSv1.0/ams.fetchTemplateData.do?template=TemplateJ&page=PVPOForms, and is herein incorporated by reference in its entirety.

The most similar variety to NUN 01307 ME is Caribbean Gold a commercial variety from Rijk Zwaan, whereas similar variety Olympic Gold is a variety from Sakata Seed. In Table 1 a comparison between NUN 01307 ME and most similar variety Caribbean Gold and similar variety Olympic Gold is shown based on a trial in the USA. Trial location: Acampo Calif. USA, (coordinates: 38°07'261"N, −121°18'80547"W), USA 2011. Average temperatures for the day were 33.1° C. and 14.7° C. for the night. Planting date: 20 Jun. 2011. Drip irrigation.

Two replications of 50 plants each, from which 20 plants or plant parts were randomly selected to measure characteristics. In Table 1 the USDA descriptors of NUN 01307 ME (this application) and reference Caribbean Gold (commercial variety) and Olympic Gold (commercial variety) are summarized.

TABLE 1 morphological and/or physiological characteristics of NU 01307 ME and comparative varieties, including distinguishing characteristics of NUN 01307 ME (in bold)

| Descriptor | Application Variety NUN 01307 ME | Comparison Variety Caribbean Gold | Comparison Variety Olympic Gold |
|---|---|---|---|
| 1. TYPE: | 5 | 5 | 5 |
| 1 = Persian 2 = Honey Dew | | | |
| 3 = Casaba 4 = Crenshaw | | | |
| 5 = Common or Summer | | | |
| 6 = Other _____ . | | | |
| 2. AREA OF BEST ADAPTATION IN U.S.A.: | 4 | 4 | 4 |
| 1 = Southeast 2 = Northeast/North Central 3 = Southwest | | | |
| 4 = Most Areas | | | |
| 3. MATURITY: | 92 | 80 | 86 |
| Days From Seeding to Harvest | | | |
| 4. PLANT: | | | |
| Fertility: | 1 | 1 | 1 |
| 1 = Andromonoecious 2 = Monoecious 3 = Gynoecious | | | |
| 4 = Other _____ | | | |
| Habit: | 1 | 1 | 1 |
| 1 = Vine 2 = Semi-bush 3 = Bush | | | |
| 5. LEAF: (Mature Blade of Third Leaf) | | | |
| Shape: | 3 | 3 | 3 |
| 1 = Orbicular 2 = Ovate 3 = Reniform (Cordate) | | | |
| Lobes: | 2 | 2 | 2 |
| 1 = Not Lobed 2 = Shallowly Lobed 3 = Deeply Lobed | | | |
| Color: | 2 | 2 | 3 |
| 1 = Light Green (Honey Dew) | | | |
| 2 = Medium Green | | | |
| 3 = Dark Green (Rio Gold) | | | |
| Color Chart Name | RHS | RHS | RHS |
| Color Chart Code (GG = Green Group; YGG = Yellow Green Group) | N137A | 137B | 147B |
| Length mm | 105.5 | 120.3 | 123.2 |
| Width mm | 132.3 | 142.2 | 140.3 |
| Surface: | 3 | 3 | 3 |
| 1 = Pubescent 2 = Glabrous 3 = Scabrous | | | |

TABLE 1-continued morphological and/or physiological characteristics of NU 01307 ME and comparative
varieties, including distinguishing characteristics of NUN 01307 ME (in bold)

| Descriptor | Application Variety NUN 01307 ME | Comparison Variety Caribbean Gold | Comparison Variety Olympic Gold |
|---|---|---|---|
| 6. FRUIT: | (at Edible Maturity): | | |
| Length in cm | 13.4 | 13.7 | 13.8 |
| Diameter in cm | 13.1 | 12.3 | 12.4 |
| Weight in g | 1320 | 1343 | 1344 |
| Shape: 1 = Oblate 2 = Oval 3 = Round 4 = Elongate-Cylindrical 5 = Spindle 6 = Acorn | 2 | 2 | 2 |
| Surface: 1 = Smooth 2 = Netted 3 = Corrugated 4 = Warted | 2 | 2 | 2 |
| Blossom Scar: 1 = Obscure 2 = Conspicuous | 1 | 1 | 1 |
| Rib Presence: 1 = Absent 2 = Present | 1 | 1 | 1 |
| No. Ribs per Fruit | N.A. | N.A. | N.A. |
| Rib Width at Medial in mm | N.A. | N.A. | N.A. |
| Ribs Surface: 1 = Smooth 2 = Netted | N.A. | N.A. | N.A. |
| Suture Depth: 1 = Shallow (Golden Delight) 2 = Medium 3 = Deep (Hackensack) | N.A. | N.A. | N.A. |
| Suture Surface: 1 = Smooth 2 = Netted | N.A. | N.A. | N.A. |
| Shipping Quality: 1 = Poor (Home Garden) 2 = Fair (Short Distance Shipping) 3 = Excellent (Long Distance Shipping) | 3 | 3 | 2 |
| Fruit Abscission: 1 = When Ripe 2 = When Overripe 3 = Do Not Abscise | 3 | 3 | 1 |
| 7. RIND NET: | | | |
| Net Presence: 1 = Absent 2 = Sparse 3 = Abundant | 3 | 3 | 3 |
| Distribution: 1 = Spotty 2 = Covers Entire Fruit | 2 | 2 | 2 |
| Coarseness: 1 = Fine 2 = Medium Coarse 3 = Very Coarse | 2 | 2 | 2 |
| Interlacing: 1 = None 2 = Some 3 = Complete | 3 | 3 | 3 |
| Interstices: 1 = Shallow 2 = Medium Deep 3 = Deep | 2 | 2 | 2 |
| 8. RIND TEXTURE: | | | |
| Texture: 1 = Soft 2 = Firm 3 = Hard | 3 | 3 | 3 |
| Thickness at Medial in mm | 3.4 | 3.4 | 2.9 |
| 9. RIND COLOR: | 01 = White 02 = Cream 03 = Buff 04 = Yellow 05 = Gold 06 = Green 07 = Magenta 08 = Bronze 09 = Brown 10 = Gray 11 = Black 12 = Other (Specify) | | |
| Color Chart Name | RHS | RHS | RHS |
| Rind Color At Edible Maturity | | | |
| Primary Color/ | 04/06 | 10/06 | 06 |
| Color Chart Value | 151B | 190C | 139A |
| Mottling Color/ | N.A. | N.A. | N.A. |
| Color Chart Value | | | |
| Net Color/ | 10/04 | 10/04 | 10/04 |
| Color Chart Value | 161C | 162D | 161C |
| Furrow (Suture)/ | N.A. | N.A. | N.A. |
| Color Chart Value | | | |
| Rind Color At Full Maturity | | | |
| Primary Color/ | 07 | 03 | 07 |
| Color Chart Value | 17C | 160D | N25D |
| Mottling Color/ | N.A. | N.A. | N.A. |
| Color Chart Value | | | |
| Net Color/ | 04/01 | 04/01 | 04/10 |
| Color Chart Value | 158A | 159C | 159D |
| Furrow (Suture)/ | N.A. | N.A. | N.A. |
| Color Chart Value | | | |

TABLE 1-continued morphological and/or physiological characteristics of NU 01307 ME and comparative varieties, including distinguishing characteristics of NUN 01307 ME (in bold)

| Descriptor | Application Variety NUN 01307 ME | Comparison Variety Caribbean Gold | Comparison Variety Olympic Gold |
|---|---|---|---|
| 10. FLESH (At Edible Maturity): | 01 = White 02 = Cream 03 = Yellow 04 = Green 05 = Magenta 06 = Salmon 07 = Pink 08 = Other (Magenta) | | |
| Color Chart Name | RHS | RHS | RHS |
| Color Near Cavity/ | 08 | 05/06 | 05/06 |
| Color Chart Value | 30A | 25C | 25C |
| Color in Center/ | 08 | 05/06 | 05/06 |
| Color Chart Value | 30A | 25C | 25C |
| Color Near Rind/ | 03/04 | 03/04 | 03/04 |
| Color Chart Value | 145A | 145A | 145A |
| Refractometer % Soluable Solids (Center of Flesh) | 14.3 | 14.8 | 12.6 |
| Aroma: 1 = Absent 2 = Faint 3 = Strong | 1 | 1 | 2 |
| Flavor: 1 = Mild 2 = Somewhat Spicy 3 = Very Spicy | 3 | 1 | 2 |
| 11. SEED CAVITY: | | | |
| Length in mm | 80.9 | 92.8 | 88.2 |
| Width in mm | 50.8 | 60.6 | 57.1 |
| Shape in X-Section: 1 = Circular 2 = Triangular | n.r. | n.r. | n.r. |
| 12. SEEDS: | | | |
| No. Seeds per Fruit | 600 | 480.6 | 461.2 |
| gm per 1,000 Seeds | 33.0 | 26.5 | 31.2 |
| 13. DISEASE RESISTANCE: | 0 = not tested; 1 = susceptible, 2 = resistant | | |
| Bacterial Wilt | 0 | 0 | 0 |
| Root Rot | 0 | 0 | 0 |
| Crown Blight | 0 | 0 | 0 |
| Melon Rust | 0 | 0 | 0 |
| Powdery Mildew | 2 *Erysiphe cichoracearum*, *Sphaerotheca fuliginea* (races 1 and 2) | 2 *Sphaerotheca fuliginea* (races 1 and 2) | 0 |
| *Verticillum* Wilt | 0 | 0 | 0 |
| Sulphur Burn | 0 | 0 | 0 |
| Scab | 0 | 0 | 0 |
| Watermelon Mosaic | 0 | 0 | 0 |
| Downy Mildew | 0 | 0 | 0 |
| *Fusarium* Wilt | 2 (races 0, 1 and 2) | 0 | 0 |
| Root Knot (Nematode) | 0 | 0 | 0 |
| Anthracnose | 0 | 0 | 0 |
| Cucumber Mosiac | 0 | 0 | 0 |
| Squash Mosaic | 0 | 0 | 0 |
| Other (specify) _____ | 0 | 0 | 0 |
| 14. INSECT RESISTANCE: | 0 = not tested; 1 = susceptible, 2 = resistant | | |
| Aphid | 0 | 2 (Cotton aphid) | 0 |
| Pickle Worm | 0 | 0 | 0 |
| Darkling Ground Beetle | 0 | 0 | 0 |
| Banded Cucumber Beetle | 0 | 0 | 0 |
| Mite | 0 | 0 | 0 |
| Western Spotted Cucumber Beetle | 0 | 0 | 0 |
| Melon Leafhopper | 0 | 0 | 0 |
| Melon Worm | 0 | 0 | 0 |
| Western Striped Cucumber Beetle | 0 | 0 | 0 |
| Melon Leafminer | 0 | 0 | 0 |
| Other (Specify) _____ | 0 | 0 | 0 |

These are typical values. Values may vary due to environment. Other values that are substantially equivalent are also within the scope of the invention.
N.A. = not applicable;
n.r. = not recorded.

The invention claimed is:

1. A seed of melon variety NUN 01307 ME, wherein a representative sample of said seed has been deposited under Accession Number NCIMB 42204.

2. A plant of melon variety NUN 01307 ME, or a part thereof, wherein a representative sample of seed of said variety has been deposited under Accession Number NCIMB 42204.

3. A fruit of melon variety NUN 01307 ME, or a plant part produced from the plant of claim 2.

4. A method of producing a melon plant, comprising crossing the plant of claim 2 with a second melon plant one or more times, and selecting progeny from said crossing.

5. A method of producing a melon plant, comprising selfing the plant of claim 2 one or more times, and selecting progeny from said selfing.

6. Progeny of melon variety NUN 01307 ME obtained by further breeding with said variety, wherein a representative sample of seed of NUN 1307 ME has been deposited under Accession Number NCIMB 42204.

7. The progeny of claim 6, wherein said progeny have all the physiological and morphological characteristics of melon variety NUN 01307 ME when grown under the same environmental conditions.

8. An Essentially Derived Variety of NUN 01307 ME having one, two or three physiological and/or morphological characteristics which are different from those of NUN 01307 ME and which otherwise has all the physiological and morphological characteristics of NUN 01307 ME, wherein a representative sample of seed of variety NUN 01307 ME has been deposited under Accession Number NCIMB 42204.

9. A method of producing plants, or a part thereof, of variety NUN 01307 ME comprising vegetative propagation of variety NUN 01307 ME, wherein a representative sample of seed of NUN 1307 ME has been deposited under Accession Number NCIMB 42204.

10. The method of claim 9, wherein said vegetative propagation comprises regenerating a whole plant from a part of variety NUN 01307 ME.

11. The method of claim 10, wherein said part is a cutting, a cell culture or a tissue culture.

12. A vegetative propagated plant of variety NUN 01307 ME, or a part thereof, having all the morphological and physiological characteristics of NUN 01307 ME when grown under the same environmental conditions, wherein a representative sample of seed of NUN 1307 ME has been deposited under Accession Number NCIMB 42204.

13. Plant part derived from variety NUN 01307 ME, or from a plant of claim 12, wherein said plant part are harvested fruit or parts thereof, pollen, cells, leaves or parts thereof, petioles, shoots or parts thereof, stems or parts thereof, roots or parts thereof, cuttings, or flowers or parts thereof.

14. A food or feed product comprising a plant part of claim 13.

15. The food or feed product of claim 14, wherein said plant part is fresh or processed.

16. A melon plant produced by growing the seed of claim 1.

17. A method of producing a melon plant having a desired trait, wherein the method comprises transforming the melon plant of claim 2 with a transgene that confers the desired trait, wherein the transformed plant retains all the phenotypic and morphological characteristics of variety NUN 01307 ME and contains the desired trait, a representative sample of seed of said variety NUN 01307 ME having been deposited under Accession Number NCIMB 42204.

18. A melon plant produced by the method of claim 17, wherein the plant comprises the desired trait and all of the physiological and morphological characteristics of NUN 01307 ME.

19. A cell or tissue culture produced from a plant of claim 2.

20. A melon plant regenerated from a cell or tissue culture of claim 19, said plant expressing all the morphological and physiological characteristics of NUN 01307 ME, wherein a representative sample having been deposited under Accession Number NCIMB 42204.

21. A melon plant comprising at least a first set of the chromosomes of melon line NUN 01307 ME, a sample of seed of said line having been deposited under Accession Number NCIMB 42204 and further comprising a single locus conversion, wherein said plant has essentially all of the morphological and physiological characteristics of the plant comprising at least a first set of the chromosomes of melon line NUN 01307 ME.

22. The plant of claim 21, wherein the single locus conversion confers a trait selected from the group consisting of male sterility, herbicide tolerance, insect resistance, pest resistance, disease resistance, environmental stress tolerance, modified carbohydrate metabolism and modified protein metabolism.

* * * * *